(12) United States Patent
Ryan

(10) Patent No.: US 11,328,621 B2
(45) Date of Patent: *May 10, 2022

(54) DIETARY REGIME FOR TREATMENT OF ACNE AND OTHER INFLAMMATORY SKIN CONDITIONS

(71) Applicant: Red Pinnace Limited, Hong Kong (CN)

(72) Inventor: Marie Helen Ryan, Vientiane (LA)

(73) Assignee: Red Pinnace Limited, Hong Kong (CN)

( * ) Notice: Subject to any disclaimer, the term of this patent is extended or adjusted under 35 U.S.C. 154(b) by 51 days.

This patent is subject to a terminal disclaimer.

(21) Appl. No.: 16/871,959

(22) Filed: May 11, 2020

(65) Prior Publication Data

US 2020/0335008 A1    Oct. 22, 2020

Related U.S. Application Data

(63) Continuation-in-part of application No. 15/031,852, filed as application No. PCT/IB2014/002312 on Oct. 27, 2014, now Pat. No. 10,650,064.

(60) Provisional application No. 61/895,434, filed on Oct. 25, 2013.

(51) Int. Cl.
| | |
|---|---|
| *A23L 33/00* | (2016.01) |
| *G09B 19/00* | (2006.01) |
| *G09B 5/02* | (2006.01) |
| *G16H 20/60* | (2018.01) |
| *G06Q 30/06* | (2012.01) |

(52) U.S. Cl.
CPC .......... *G09B 19/0092* (2013.01); *A23L 33/30* (2016.08); *A23L 33/40* (2016.08); *G06Q 30/0633* (2013.01); *G09B 5/02* (2013.01); *G16H 20/60* (2018.01); *A23V 2002/00* (2013.01)

(58) Field of Classification Search
None
See application file for complete search history.

(56) References Cited

U.S. PATENT DOCUMENTS

2008/0059342 A1    3/2008    Culver et al.

FOREIGN PATENT DOCUMENTS

| CN | 1228705 A | 9/1999 |
| CN | 101228901 A | 7/2008 |
| EP | 1597978 A1 | 11/2005 |
| WO | WO 1998/04270 A1 | 2/1998 |

OTHER PUBLICATIONS

Schaefer, et al. Abstract, "Prevalence of skin diseases in a cohort of 48,665 employees in Germany". Published in Dermatology, 2008; 217 (2):169-72. (Year: 2008).*
IP Australia, Examination Report dated Mar. 9, 2019 in Australian Patent Application No. 2014338690, 7 pages.
European Patent Office, Extended Search Report dated Jun. 6, 2017 in European Patent Application No. EP14856580.7, 6 pages.
ISA CN, International Search Report dated Mar. 10, 2015 in International Application No. PCT/IB2014/002312, 4 pages.
Katta, Rajani, M.D. et al., "Diet and Dermatology, The Role of Dietary Internention in Skin Disease," *J Clin Aesthet Dermatology*, vol. 7, No. 7, Jul. 16, 2014, pp. 46-51, 6 pages.
Reddit, "An Apple a day brings my skin decay. It's Fructose!," posted Dec. 27, 2012, https://www.reddit.com/r/acne/comments/15ip0b/an_apple_a_day_brings_my_skin_its_fructose/, downloaded Oct. 5, 2017, 4 pages.
Acne Research: "The Superoxide Dismutase Theory". Available online as of Sep. 1, 2012 from https://acneresearch.org. pp. 1-5. (Year: 2012).
"FODMAPS: How Healthy Foods Can Cause Acne". Available online as of Jul. 6, 2012 from www.acneeinstein.com. pp. 1-10. (Year: 2012).
"The Gut-Skin Axis". Available online as of May 14, 2012 from www.acneeinstein.com. pp. 1-11. (Year: 2012).
Gibson, Peter R., M.D. et al., "Food Choice as a Key Management Strategy for Functional Gastrointestinal Symptoms," *The American Journal of Gastroenterology*, vol. 107, May 3, 2012, pp. 657-666, 10 pages.
The Primal Parent: "IBS, Depression and Skin Problems in Fructose Malabsorption". Available as of Mar. 31, 2012 from http://theprimalparent.com. pp. 1-50 (Year: 2012).
Veith, W.B. et al., "The Association of Acne Vulgaris With Diet," *Cutis*, Aug. 2011 88(2) 84-91, 8 pages.
Mercola—"The Root Cause of Acne Your Doctor Will Never tell you About". Available online as of May 31, 2011 from https://articles.mercola.com. pp. 1-12. (Year: 2011).
Gibson, P.R. et al., "Evidence-based dietary management of functional gastrointestinal symptoms: The FODMAP approach," *Journal of Gastroenterology and Hepatology*, vol. 25, No. 2, Feb. 2010, pp. 252-258, 8 pages.
Melnik, B.C. et al., "Role of insulin, insulin-like growth factor-1, hyperglycaemic food and milk consumption in the pathogenesis of acne vulgaris," *Experimental Dermatology*, Oct. 2009, vol. 18, No. 10, pp. 833-841, 10 pages.
"Foods High in Fructose, Sorbitol, Fructans and FODMAPS". Available online as of Jun. 6, 2009 from www.healthhype.com. pp. 1-7. (Year: 2009).
Smith, R.N. et al/ "The effect of a low glycemic load diet on acne vulgaris and the fatty acid composition of the skin surface triglycerides," *Journal of Dermatological Science*, Apr. 2008, vol. 50, No. 1, pp. 41-52, 12 pages.
Danby, F. W., M.D. "Acne and milk, the diet myth, and beyond," *Journal of the American Academy of Dermatology*, vol. 52, Issue 2, Feb. 2005, pp. 360-362, 3 pages.

* cited by examiner

*Primary Examiner* — Jenna A Watts
(74) *Attorney, Agent, or Firm* — Masuvalley & Partners

(57) ABSTRACT

Disclosed herein is a method for preventing or controlling rosacea, psoriasis or eczema in a subject. The method comprises administering to the subject a diet that is low in fructose, oligosaccharides and/or polyol sugars.

8 Claims, 9 Drawing Sheets

Week 0 (diet 0 days) no prescribed medication

Week 2 (diet 14 days) no prescribed medication

Head

| | | | | | | | |
|---|---|---|---|---|---|---|---|
| Area | ○ 0% | ○ <10% | ○ 10-29% | ○ 30-49% | ○ 50-69% | ○ 70-89% | ○ 90-100% |
| Erythema (redness) | ○ 0 | ○ 2 | ○ 3 | ○ 4 | | | |
| Induration (thickness) | ○ 0 | ○ 2 | ○ 3 | ○ 4 | | | |
| Desqamation (scaling) | ○ 0 | ○ 2 | ○ 3 | ○ 4 | | | |

Arms

| | | | | | | | |
|---|---|---|---|---|---|---|---|
| Area | ○ 0% | ○ <10% | ○ 10-29% | ○ 30-49% | ○ 50-69% | ○ 70-89% | ○ 90-100% |
| Erythema (redness) | ○ 0 | ○ 2 | ○ 3 | ○ 4 | | | |
| Induration (thickness) | ○ 0 | ○ 2 | ○ 3 | ○ 4 | | | |
| Desqamation (scaling) | ○ 0 | ○ 2 | ○ 3 | ○ 4 | | | |

Trunk

| | |
|---|---|
| Area | ○ 0%  ○ <10%  ○ 10-29%  ○ 30-49%  ○ 50-69%  ○ 70-89%  ○ 90-100% |
| Erythema (redness) | ○ 0  ○ 2  ○ 3  ○ 4 |
| Induration (thickness) | ○ 0  ○ 2  ○ 3  ○ 4 |
| Desqamation (scaling) | ○ 0  ○ 2  ○ 3  ○ 4 |

Legs

| | |
|---|---|
| Area | ○ 0%  ○ <10%  ○ 10-29%  ○ 30-49%  ○ 50-69%  ○ 70-89%  ○ 90-100% |
| Erythema (redness) | ○ 0  ○ 2  ○ 3  ○ 4 |
| Induration (thickness) | ○ 0  ○ 2  ○ 3  ○ 4 |
| Desqamation (scaling) | ○ 0  ○ 2  ○ 3  ○ 4 |

DIETARY REGIME FOR TREATMENT OF ACNE AND OTHER INFLAMMATORY SKIN CONDITIONS

RELATED APPLICATIONS

This application is a continuation-in-part of and claims priority to U.S. patent application Ser. No. 15/031,852 filed Apr. 25, 2016 (now U.S. Pat. No. 10,650,064 issued May 12, 2020), entitled Dietary Regime For Treatment Of Acne And Other Inflammatory Skin Conditions, which is the U.S. National Phase of and claims priority to International Patent Application PCT/IB2014/002312, filed Oct. 27, 2014, entitled Dietary Regime For Treatment Of Acne And Other Inflammatory Skin Conditions, which claims benefit of and priority to U.S. Provisional Patent Application Ser. No. 61/895,434 filed Oct. 25, 2013, entitled Dietary Regime For Treatment Of Acne And Other Inflammatory Skin Conditions, all of which are hereby incorporated herein by reference in their entireties.

TECHNICAL FIELD

The present invention relates to methods for controlling or preventing rosacea, psoriasis or eczema and other inflammatory skin conditions in humans.

BACKGROUND

Inflammatory skin disorders are a wide range of conditions caused by immune system reactions that involve the skin. The underlying aetiology of many inflammatory skin disorders is still unknown or not well understood. Rosacea is a chronic skin disease that affects more than 16 million Americans. The cause of rosacea is still unknown, and there is no cure. Rosacea's trademark symptom is small, red, pus-filled bumps on the skin that are present during flare-ups. Atopic dermatitis (hereafter referred to as eczema) is an inherited, chronic inflammatory skin condition that usually appears in early childhood. Patches of skin become red, scaly and itchy. Sometimes, tiny blisters containing clear fluid can form and the affected areas of skin can weep. Psoriasis (E-R-P) is a common skin condition that speeds up the life cycle of skin cells. It causes cells to build up rapidly on the surface of the skin. The extra skin cells form scales and red patches that are itchy and sometimes painful.

Patients with inflammatory skin disorders tend to be long-term consumers of over-the-counter (OTC) preparations, pharmaceuticals and prescribed medicines. Some patients with persistent inflammatory skin disorders have been reported to experience significant psychological injury related to the chronic and disfiguring nature of the condition (3).

Unfortunately, many therapeutic interventions can cause serious adverse clinical events. In addition, the overuse of topical medications, cleansers, or astringents can often worsen a patient's condition.

There is a need for new options to prevent or treat inflammatory skin conditions that resolve the significant disadvantages of existing treatments.

SUMMARY

The present invention is predicated on the clinical finding that daily consumption of foods high in fructose, oligosaccharides and/or polyol sugars can lead to inflammatory skin conditions including acne, rosacea, psoriasis and eczema. These clinical findings are supported by the fact that acne has been rarely observed in societies that have maintained traditional diets. This effect has been noted in communities such as the Inuit of Canada (4, 5), Okinawa islanders of Japan (6), the Ache hunter gatherers of Indonesia, and the Kitavan islanders of Papua New Guinea (6). The absence of acne in these populations clearly suggests the potential for underlying genetic or environmental factors, including diet.

In a first aspect, the present invention provides a method for preventing or controlling rosacea, psoriasis or eczema in a subject, the method comprising administering to the subject a diet that is low in fructose, oligosaccharides and polyol sugars.

In embodiments, the diet that is low in fructose, oligosaccharides and polyol sugars contains 40 g or less per day of fructose, oligosaccharides and polyol sugars.

Embodiments of the first aspect of the invention may also comprise providing one or more food product(s) in accordance with the formulated diet.

Embodiments of the first aspect may also comprise obtaining dietary information from the subject wherein said dietary information includes details of the subject's diet over a period of time; assessing the dietary information to determine the total daily content of fructose, oligosaccharides and polyol sugars in the subject's diet and/or determining whether one or more foodstuffs in the subjects diet is high in fructose, oligosaccharides and polyol sugars; prescribing to the subject the diet that has a cumulative daily total of 40 g or less of fructose, oligosaccharides and polyol sugars; and administering to the subject the diet that has a cumulative daily total of 40 g or less of fructose, oligosaccharides and polyol sugars.

In a second aspect, the present invention provides a method for treating or preventing rosacea, psoriasis or eczema in a subject, the method comprising: viewing a list of food products forming part of a diet; selecting one or more food product(s) from the list to form a daily diet list; calculating the total content of fructose, oligosaccharides and polyol sugars contained in the foodstuffs on the daily diet list; providing feedback to the subject as to whether the foodstuffs on the daily diet list contain a total amount of fructose, oligosaccharides and polyol sugars of 40 g or less per day; and, if the amount of fructose, oligosaccharides and polyol sugars in the food product(s) on the daily diet list is below 40 g or less per day, creating a customised daily diet for the subject; and administering to the subject the customised daily diet.

Embodiments of the second aspect may also comprise ordering at least some of the food product(s) in the customised daily diet for the subject.

In certain embodiments of the second aspect the list of food products forming part of the diet are contained on a database of information relating to the content of fructose, oligosaccharides and polyol sugars in the food products; the database residing on a server computer; a user interface accessible by a subject and in communication with the database via a communication device, the user interface allowing the subject to select one or more food product(s) from the database; a processor for calculating the total content of fructose, oligosaccharides and polyol sugars in the selected one or more food product(s); and an output for displaying the total content of fructose, oligosaccharides and polyol sugars in the selected one or more food product(s) to the subject.

In a third aspect, the present invention provides a method for assisting a subject to prevent or control rosacea, psoriasis or eczema, the method comprising: obtaining dietary information from the subject wherein said dietary information includes details of the subject's diet over a period of time; assessing the dietary information to determine the total daily content of fructose, oligosaccharides and/or polyol sugars in the subject's diet and/or determining whether one or more foodstuffs in the subject's diet is high in fructose, oligosaccharides and/or polyol sugars; and prescribing to the subject a diet that is low in fructose, oligosaccharides and/or polyol sugars.

In a fourth aspect, the present invention provides a method for selecting food products for a diet for preventing or controlling rosacea, psoriasis or eczema, the method comprising: viewing a list of food products forming part of the diet; selecting one or more food product(s) from the list to form a daily diet list; calculating the total content of fructose, oligosaccharides and/or polyol sugars contained in the foodstuffs on the daily diet list; providing feedback to the subject as to whether the foodstuffs on the daily diet list contain a total amount of fructose, oligosaccharides and/or polyol sugars relative to a threshold daily value; and, if the amount of fructose, oligosaccharides and/or polyol sugars in the food product(s) on the daily diet list is below the threshold daily value, creating a customised daily diet for the subject.

In embodiments, the method of the fourth aspect further includes ordering at least some of the food product(s) in the customised daily diet for the subject. In embodiments, the ordering comprises communicating a food product(s) order to a merchant remote from the communication device. In embodiments, the ordering also comprises ordering the food product(s) from the food product(s) order from a production and/or storage facility and shipping the food product(s) to the subject.

Any one or more of the steps of the method of the fourth aspect may be implemented on a computer. For example, the list of food products forming part of the diet may be viewed on a display of a communication device, selection of the one or more food product(s) from the list to form a daily diet list may be carried out using a user interface of a communication device, and/or providing feedback to the subject may be carried using a user interface of a communication device.

In a fifth aspect, the present invention provides a database of information relating to the content of fructose, oligosaccharides and/or polyol sugars in a plurality of food products residing on a server computer; a user interface accessible by a subject and in communication with the database via a communication device, the user interface allowing the subject to select one or more food product(s) from the database; a processor for calculating the total content of fructose, oligosaccharides and/or polyol sugars in the selected one or more food product(s); and an output for displaying the total content of fructose, oligosaccharides and/or polyol sugars in the selected one or more food product(s) to the subject.

In a sixth aspect, the present invention provides a packaged foodstuff wherein the packaging of the foodstuff contains information or refers to information regarding the diet referred to in any one of the first to fifth aspects.

In an seventh aspect, the present invention provides a foodstuff in conjunction with information relating to the diet referred to in any one of the first to fifth aspects.

BRIEF DESCRIPTION OF THE FIGURES

Embodiments of the present invention will be discussed with reference to the accompanying drawings wherein.

DETAILED DESCRIPTION

Figure 1:
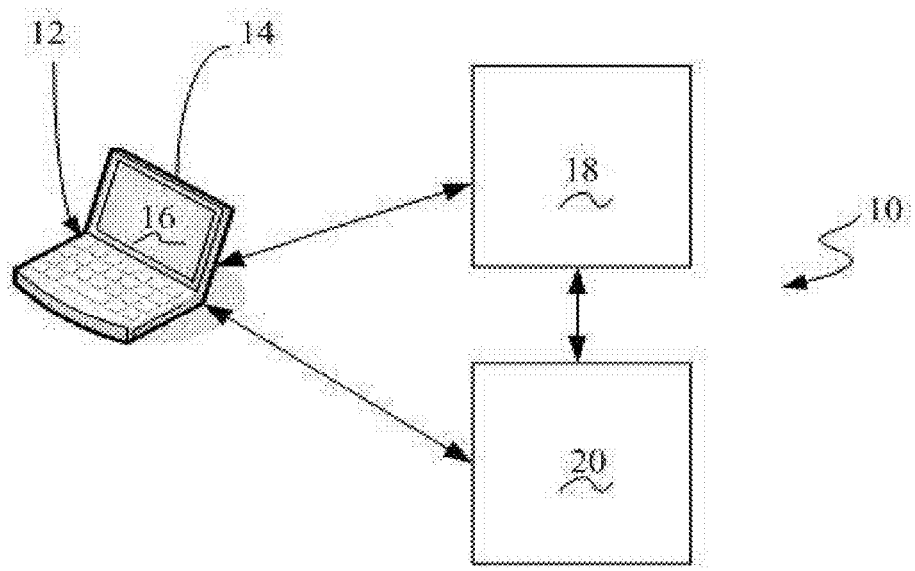
FIG. 1 is a schematic diagram of a system for creating a customised daily diet in accordance with embodiments of the invention.

The present invention, and embodiments thereof, will now be described in more detail. For ease of description, reference will be made to the treatment or prevention of acne. However, this is for illustrative purposes only and it is intended that the embodiments and aspects described can also be used in the treatment or prevention of other inflammatory skin disorders.

Before proceeding it is important to note that various terms that will be used throughout the specification have meanings that will be well understood by a skilled addressee. However, for ease of reference some of these terms will now be defined.

As used herein, the term "a diet that is low in fructose, oligosaccharides and/or polyol sugars" means a diet having a total content of fructose, oligosaccharides and/or polyol sugars that is lower than the conventional or typical diet of the subject. In embodiments, the diet that is low in fructose, oligosaccharides and/or polyol sugars contains 40 g or less per day of fructose, oligosaccharides and/or polyol sugars. However, for some subjects that amount of 40 g or less may not be low enough for the subject to prevent or control an inflammatory skin disorder. In those subjects, the individual tolerance limits in order to prevent or control an inflammatory skin disorder may need to be determined empirically. However, it is expected that the threshold level of 40 g or less will be suitable for the majority of subjects.

As used herein, the term "oligosaccharide" means a saccharide containing typically three to ten sugar units. Examples of oligosaccharides commonly found in the diet include fructans and galactans. Fructo-oligosaccharides (FOS) are found naturally in many vegetables, while inulin is a polysaccharide with a similar molecular structure to FOS but with a higher degree of polymerization.

As used herein, the term "polyol sugar" means a hydrogenated carbohydrate or sugar alcohol. Examples include xylitol, maltitol, sorbitol, erythritol, lactitol, and isomalt.

As used herein, the term "inflammatory skin disorder" is intended to include within its scope acne vulgaris, acne rosacea, general erythema, poikaderma de Civette, eczema and other conditions resulting from inflammation of the skin.

As used herein, the term "acne" is intended to include within its scope acne vulgaris and acne rosacea.

As used herein, the term "food" or "food product" means any solid or liquid material containing nutrients such as carbohydrates, proteins, and fats that are required by humans in order to obtain energy and grow.

As used herein, the term "beverage" refers to any liquid material containing water as a constituent that provides humans with the hydration necessary for normal metabolism.

As discussed, the present invention is predicated on a finding that daily consumption of foods high in fructose, oligosaccharides and/or polyol sugars can lead to inflammatory skin disorders such as acne, rosacea, psoriasis or eczema. Recent research by others (8) has suggested an association between a low-glycemic diet with reduced sebum production and fewer acne lesions. This research did not confirm an absence of acne but fewer lesions due to a low-glycemic diet. Subsequent research (9) in 2010 found no association with acne and a low-glycemic diet. In 2006 published research (10) explored gastrointestinal symptoms resulting from the consumption of rapidly fermentable, short-chain carbohydrates (simple sugars). Based on the above evidence of the present research has shown that a low tolerance to specific simple sugars other than glucose in susceptible individuals is linked to acne development rather than a generalised consumption of high-glycemic foods.

Modern diets that include a high level of processed foods can lead to an increased consumption of specific simple sugars or their modified variants. These are present, for example, in wheat, barley or rye grains, natural sweeteners, food additives, thickeners or binding agents. The present research has shown that sensitive people who consume an excess of specific simple sugars are likely to experience a rapid gastrointestinal response that precipitates (for example) in an acne flare-up. For people with persistent acne or other inflammatory skin diseases, constant minor irritation of the small intestine due to daily consumption of a range of common foods maintains a simple sugar load higher than can be tolerated for these individuals.

Certain other food additives (for example MSG) can, during periods of lowered resistance, add to the gastrointestinal discomfort and contribute to effect of the malabsorption of specific simple sugars.

It is proposed that malabsorption in the small intestine of certain groups of short-chain carbohydrates (simple sugars)

from both natural or processed sources affects the balance of gut biota. An imbalance in an individual's normal gut biota combined with the consumption of certain simple sugars, promotes the release of endotoxins that are capable of permeating the intestinal mucosa. The endotoxins migrate into the general circulatory system thereby activating an inflammatory response (11). This mechanism can lead to inflammation of skin and in susceptible individuals for example this may present as rosacea, psoriasis or eczema. This effect is pre-empted when individual tolerances for specific simple sugar load have been exceeded. Sensitivity is also exacerbated in these individuals when healthy resistance is lowered (such as hormonal fluctuations, parasite infestation or gastro-intestinal infections etc.) or by consuming certain food additives such as MSG that may irritate the small intestine. An inflammatory reaction, such as rosacea, psoriasis or eczema, is likely particularly when any of the above factors coincide.

As such, the present invention provides a method for preventing or controlling inflammatory skin diseases in a subject, the method comprising administering to the subject a diet that is low in fructose, oligosaccharides and/or polyol sugars.

A diet that is low in fructose, oligosaccharides and/or polyol sugars can be devised by determining the amounts of fructose, oligosaccharides and/or polyol sugars in food product(s) to be consumed by the subject and adjusting the diet so that the total amount of fructose, oligosaccharides and/or polyol sugars consumed by the subject is 40 g or less per day. The amounts of fructose, oligosaccharides and/or polyol sugars in food product(s) will usually be determined by determining the amounts of fructose, fructans, galactans, xylitol, maltitol, sorbitol, erythritol, lactitol, and isomalt in the food product(s).

The diet that is low in fructose, oligosaccharides and/or polyol sugars may comprise natural or commercially available foodstuffs, foodstuffs that are specifically formulated for the diet, dietary supplements, and combinations of any of these.

A suitable diet will typically include foodstuffs:
  containing complex carbohydrates in the form of grains, flakes, flours and meals from cereal grains or vegetables that are low in fructose, oligosaccharides and/or polyol sugars. Examples include flax seed, oats, corn and polished rice; and/or
  containing proteins, vitamins, minerals, carbohydrates, (simple and complex), insoluble dietary fibre, and soluble dietary fibre; and/or
  containing simple carbohydrates sourced from fruit, vegetables, grains or similar that have low levels of simple sugars particularly fructose, fructans, oligosaccharides and polyols. For example simple sugars may be selected from the group consisting of, but not limited to, rice syrup, sucrose, lactose, glucose, dextrose, stevia or other sources containing simple sugars with a higher glucose to fructose ratio.

The diet may comprise food and beverage products that are specifically formulated and manufactured for use in the diet. Suitable food and beverage products include but are not limited to: breakfast cereals, nutritional bars, snack cakes, chips, shakes, soups, soup mixes, pasta (fresh and/or dried), noodles (fresh and/or dried), ice cream, yoghurt, sorbet, beverage mixes, and beverages.

Food and beverage products that are specifically formulated and manufactured for the diet may comprise proteins, vitamins, minerals, carbohydrates, (simple and complex) and incorporate a blend of soluble and insoluble dietary fibres, and fats in appropriate amounts. The food and beverage products will normally be formulated using carbohydrates that are low in simple sugars to avoid gastro-intestinal distress that can lead to rosacea, psoriasis or eczema in susceptible individuals. The food and beverage products will also typically contain levels of fibre, protein and fats to promote fullness and ensure a healthy metabolism.

In addition to the above nutritional components, the food and beverage products may contain common ingredients such as colorants, preservatives/antioxidants, emulsifiers and flavorants and the like. Colorants, preservatives/antioxidants, emulsifiers and flavorants identified as safe for human consumption are referenced in the current edition of Food Chemicals Codex (FCC) published by the United States Pharmacopeia (USP).

Optionally, the food and beverage products may include pharmacologically active compounds known to have a role in the treatment of acne vulgaris, acne rosacea, general erythema or other inflammatory skin conditions for example poikaderma de Civette, psoriasis or eczema. Suitable pharmacologically active compounds include but are not limited to: prescription drugs, herbal compounds, derivatives or extracts, vitamins, minerals, fish oil, and omega-3 fatty acids.

The manufactured food and beverage products facilitate a convenient dietary regimen to prevent or control rosacea, psoriasis or eczema. To ensure a low daily consumption of simple sugars an individual can create a customised dietary regimen by replacing one or more meals, snacks or beverages with the food and beverage products that have been both nutritionally balanced and specifically formulated to prevent or control the condition.

The manufactured food and beverage products may be used singly or in combination to provide a full serving, which further enhances the subject's ability to customise their dietary regimen.

The manufactured food and beverage products may be formed by conventional techniques.

The packaging of a foodstuff suitable for use in the diet may contain information or refer to information regarding the diet. Alternatively, or in addition, the foodstuff may be provided or sold in conjunction with information relating to the diet. The information may include an indication that the foodstuff is suitable for use in the diet and/or for the control of rosacea, psoriasis or eczema. The information may also include details of the fructose, oligosaccharide and/or polyol sugar content of the product.

As discussed, I have found that consumption of the diet that is low in fructose, oligosaccharides and/or polyol sugars may lead to a reduction in the occurrence of rosacea, psoriasis or eczema in a subject or prevent occurrence of rosacea, psoriasis or eczema. Thus, the present invention also provides a method for assisting a subject to prevent or control rosacea, psoriasis or eczema, the method comprising prescribing to the subject a diet that is low in fructose, oligosaccharides and/or polyol sugars.

The methods of the invention may also comprise providing food product(s) in accordance with the formulated diet. The provided food product(s) may be packaged meals. Alternatively, or in addition, the provided food product(s) may be food beverage products specifically manufactured for the diet, as described earlier. Thus, the method may further comprise providing food product(s) for people susceptible to an inflammatory skin disorder.

Aspects of the method for preventing or controlling rosacea, psoriasis or eczema in a subject may be implemented on a computer. Thus, the present invention also provides a computer-implemented method for selecting food products for a diet for preventing or controlling an inflammatory skin disorder, the method comprising: viewing, on a display of a communication device, a list of food products forming part of the diet; selecting one or more food product(s) from the list, using a user interface of the communication device, to form a daily diet list; calculating the total content of fructose, oligosaccharides and/or polyol sugars contained in the foodstuffs on the daily diet list; providing feedback, using the user interface of the communication device, to the subject as to whether the foodstuffs on the daily diet list contain a total amount of fructose, oligosaccharides and/or polyol sugars relative to a threshold daily value; and, if the amount of fructose, oligosaccharides and/or polyol sugars in the food product(s) on the daily diet list is below the threshold daily value, creating a customised daily diet for the subject.

A simplified schematic diagram of a system 10 for creating a customised daily diet for a subject is shown in FIG. 1. The system 10 comprises a communication device 12 having a display 14, a user interface 16 displayable on the display 14, a database 18 comprising a list of food products and information relating to the content of fructose, oligosaccharides and/or polyol sugars in each of the food products, a processor 20 for calculating the total content of fructose, oligosaccharides and/or polyol sugars contained in the food product(s) on a daily diet list selected by a subject using the user interface 16 and comparing the total content of fructose, oligosaccharides and/or polyol sugars to a threshold daily value, and providing an output to the subject as to whether consumption of the food product(s) on the daily diet list are likely to prevent or control an inflammatory skin disorder in the subject.

Figure 2:
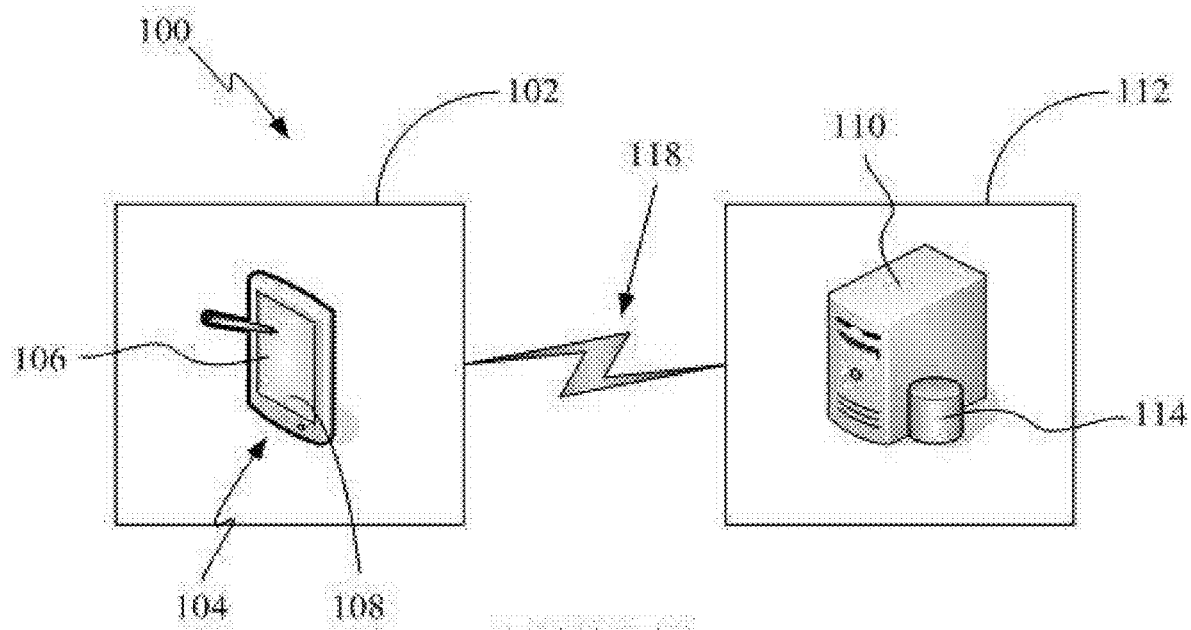
FIG. 2 is a schematic diagram of a system for creating a customised daily diet implemented across a communications network in accordance with embodiments of the invention.
Figure 3:
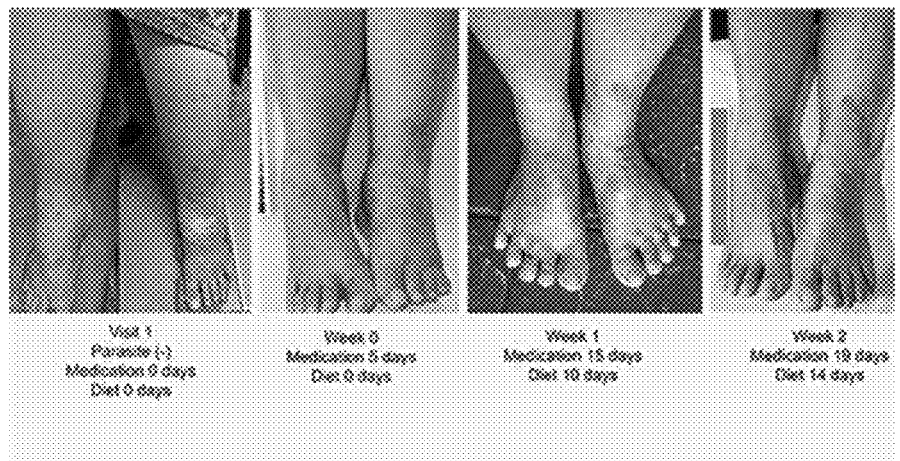
FIG. 3 shows photographs of a female subject with severe eczema at visit 1 (parasite (−); no medication), week 0 (medication 5 days; diet 0 days), week 1 (medication 15 days; diet 10 days) and week 2 (medication 19 days; diet 14 days). The overall EASI score for the subject decreased from 21.6 to 0.
Figure 4:
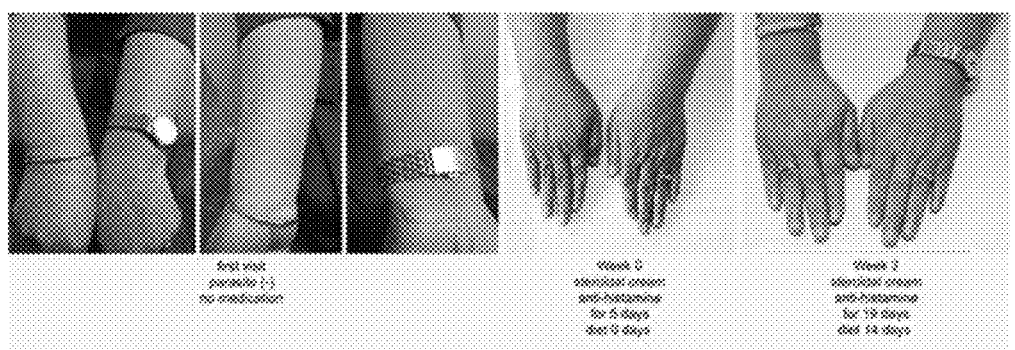
FIG. 4 shows further photographs of the female subject with severe eczema shown in FIG. 3 at visit 1 (parasite (−); no medication), week 0 (steroidal cream, antihistamine for 5 days; diet 0 days) and week 2 (steroidal cream, antihistamine for 19 days; diet 14 days). The overall EASI score for the subject decreased from 21.6 to 0.
Figure 5:
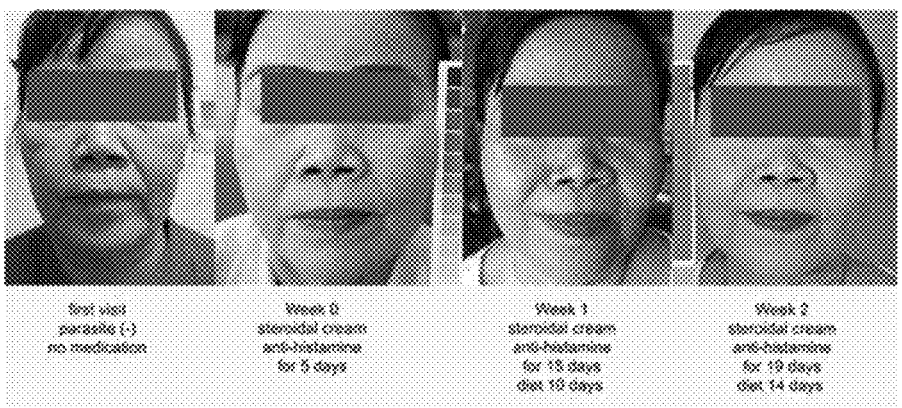
FIG. 5 shows further photographs of the subject with severe eczema shown in FIGS. 3 and 4 at visit 1 (parasite (−); no medication), week 0 (steroidal cream, antihistamine for 5 days), week 1 (steroidal cream, antihistamine for 15 days; diet 10 days) and week 2 (steroidal cream, antihistamine for 19 days; diet 14 days). The overall EASI score for the subject decreased from 21.6 to 0.
Figure 6:
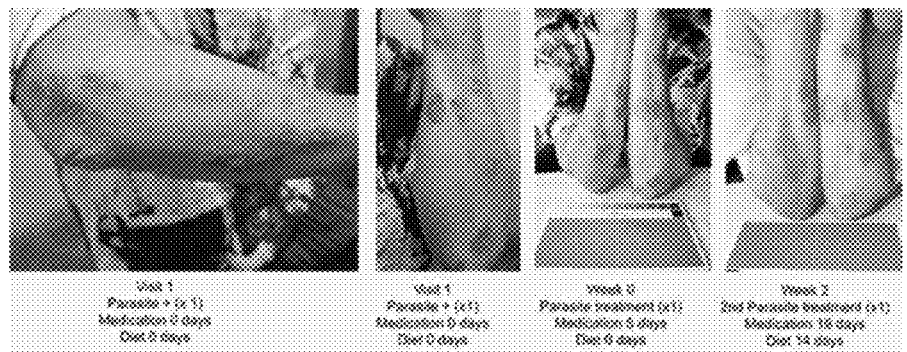
FIG. 6 shows photographs of a female subject with severe psoriasis at visit 1 (parasite (+) (×1); medication 0 days; diet 0 days), week 0 (parasite treatment (×1); medication 5 days; diet 0 days) and week 2 ($2^{nd}$ parasite treatment (×1); medication 19 days; diet 14 days). The overall PASI score for the subject decreased from 14.4 to 7.2.
Figure 7:
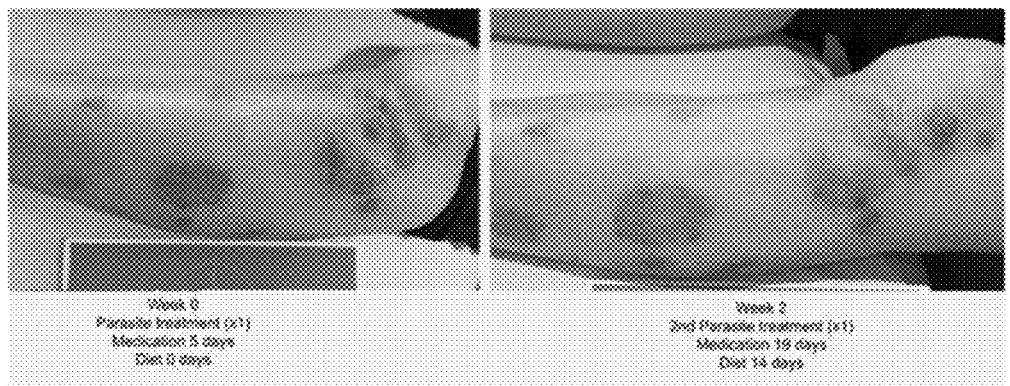
FIG. 7 shows further photographs of the female subject with severe psoriasis shown in FIG. 6 at week 0 (parasite treatment (×1); medication 5 days; diet 0 days) and week 2 ($2^{nd}$ parasite treatment (×1); medication 19 days; diet 14 days). The overall PASI score for the subject decreased from 14.4 to 7.2.
Figure 8:
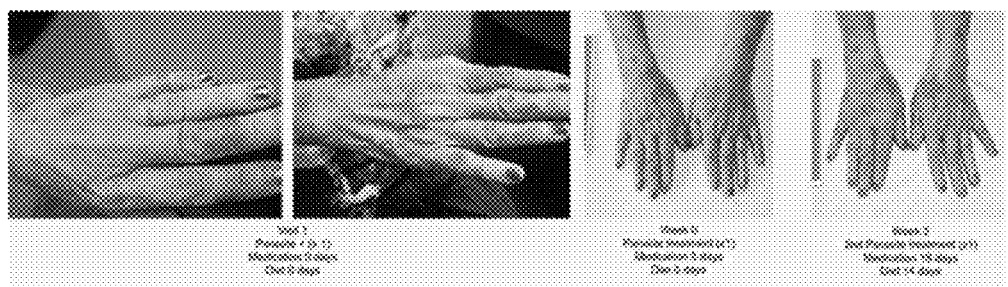
FIG. 8 shows further photographs of the female subject with severe psoriasis at shown in FIGS. 6 and 7 visit 1 (parasite (+) (×1); medication 0 days; diet 0 days), week 0 (parasite treatment (×1); medication 5 days; diet 0 days) and week 2 ($2^{nd}$ parasite treatment (×1); medication 19 days; diet 14 days). The overall PASI score for the subject decreased from 14.4 to 7.2.
Figure 9:
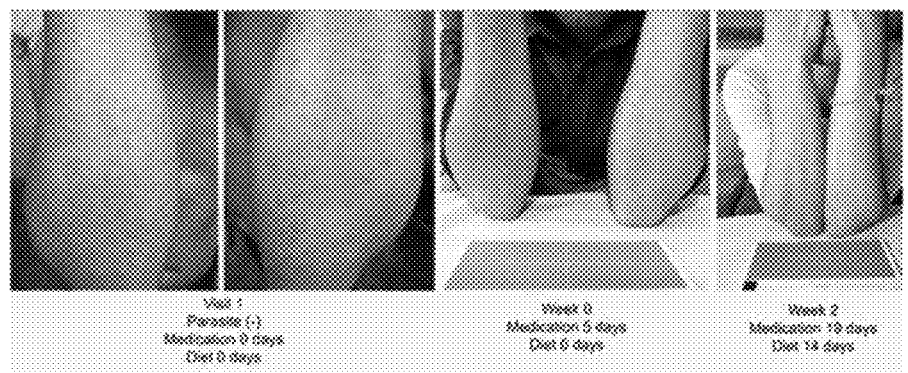
FIG. 9 shows photographs of a male subject with severe psoriasis at visit 1 (parasite (−); medication 0 days; diet 0 days), week 0 (medication 5 days; diet 0 days) and week 2 (medication 19 days; diet 14 days). The overall PASI score for the subject decreased from 24.2 to 12.6.
Figure 10:
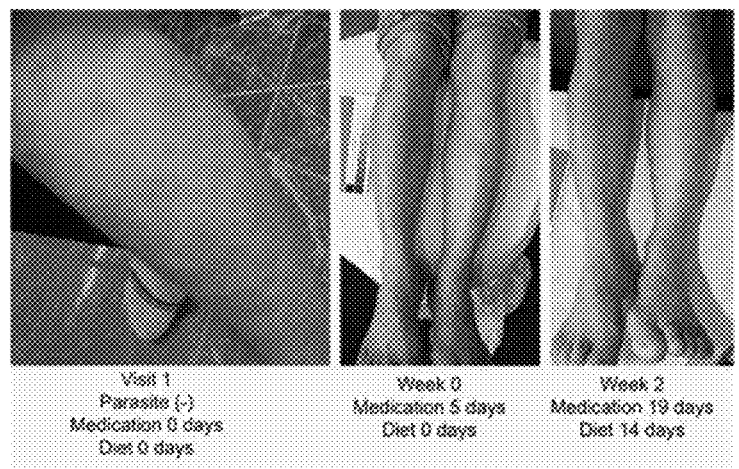
FIG. 10 shows further photographs of the male subject with severe psoriasis shown in FIG. 9 at visit 1 (parasite (−); medication 0 days; diet 0 days), week 0 (medication 5 days; diet 0 days) and week 2 (medication 19 days; diet 14 days). The overall PASI score for the subject decreased from 24.2 to 12.6.
Figure 11:
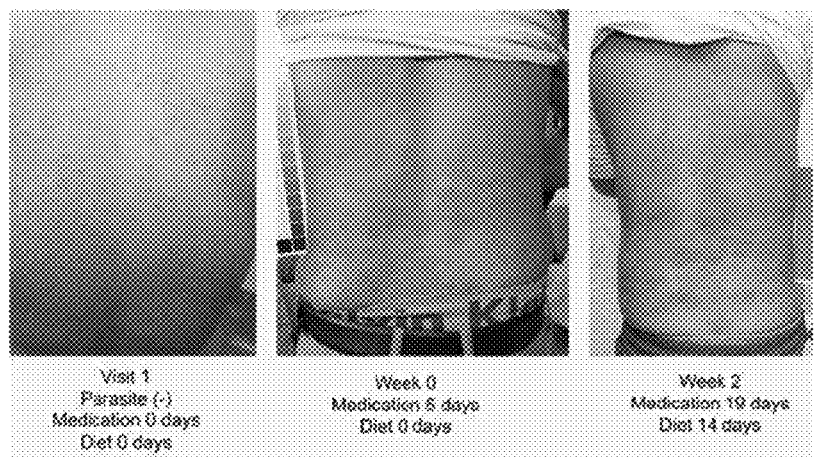
FIG. 11 shows further photographs of the male subject with severe psoriasis shown in FIGS. 9 and 10 at visit 1 (parasite (−); medication 0 days; diet 0 days), week 0 (medication 5 days; diet 0 days) and week 2 (medication 19 days; diet 14 days). The overall PASI score for the subject decreased from 24.2 to 12.6.
Figure 12:
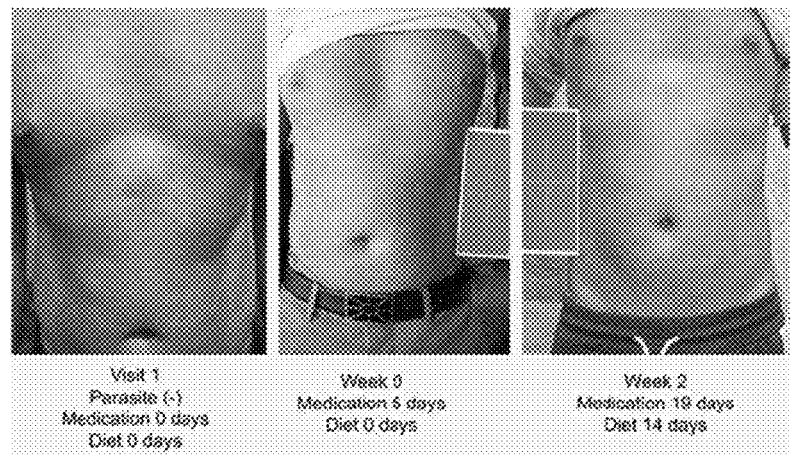
FIG. 12 shows further photographs of the male subject with severe psoriasis shown in FIGS. 9 to 11 at visit 1 (parasite (−); medication 0 days; diet 0 days), week 0 (medication 5 days; diet 0 days) and week 2 (medication 19 days; diet 14 days). The overall PASI score for the subject decreased from 24.2 to 12.6.
Figure 13:
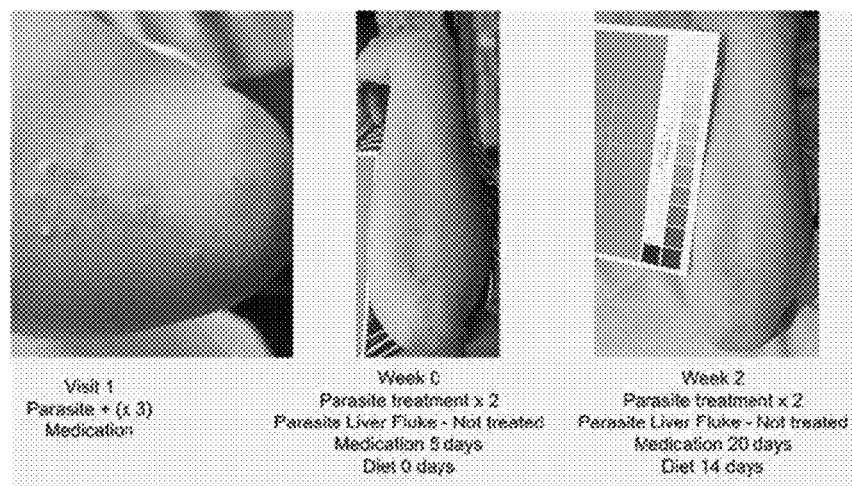
FIG. 13 shows photographs of a female subject with psoriasis at visit 1 (parasite (+) ×3; medication), week 0 (parasite treatment ×2; parasite liver fluke—not treated; medication 5 days; diet 0 days) and week 2 (parasite treatment ×2; parasite liver fluke—not treated medication 20 days; diet 14 days). The overall PASI score for the subject decreased from 5.6 to 2.8.
Figure 14:
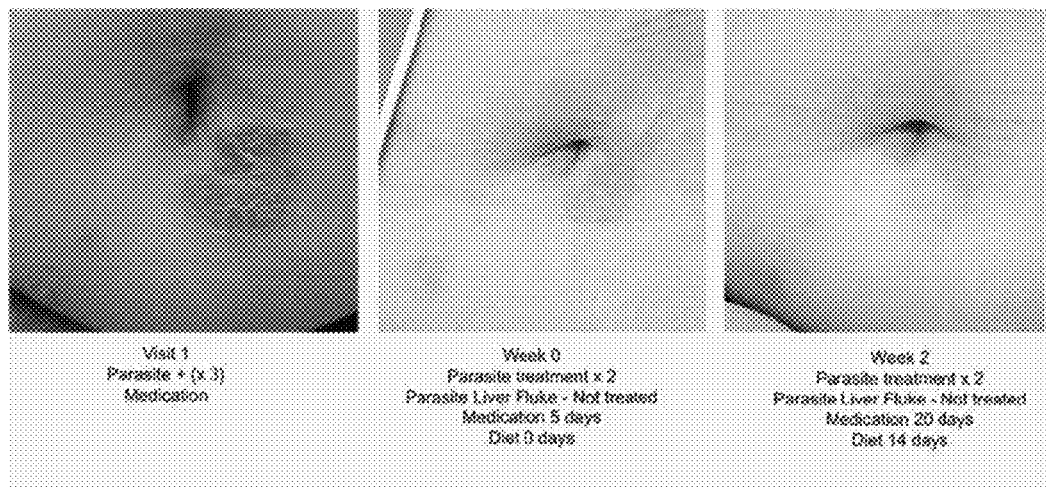
FIG. 14 shows further photographs of the female subject with psoriasis shown in FIG. 13 at visit 1 (parasite (+) ×3; medication), week 0 (parasite treatment ×2; parasite liver fluke—not treated; medication 5 days; diet 0 days) and week 2 (parasite treatment ×2; parasite liver fluke—not treated medication 20 days; diet 14 days). The overall PASI score for the subject decreased from 5.6 to 2.8.
Figure 15:
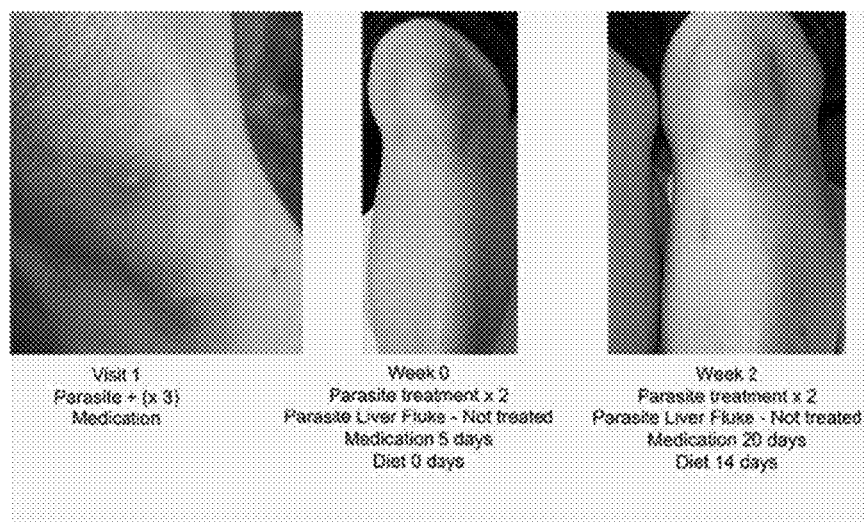
FIG. 15 shows further photographs of the female subject with psoriasis shown in FIGS. 13 and 14 at visit 1 (parasite (+) ×3; medication), week 0 (parasite treatment ×2; parasite liver fluke—not treated; medication 5 days; diet 0 days) and week 2 (parasite treatment ×2; parasite liver fluke—not treated medication 20 days; diet 14 days). The overall PASI score for the subject decreased from 5.6 to 2.8.
Figure 16:
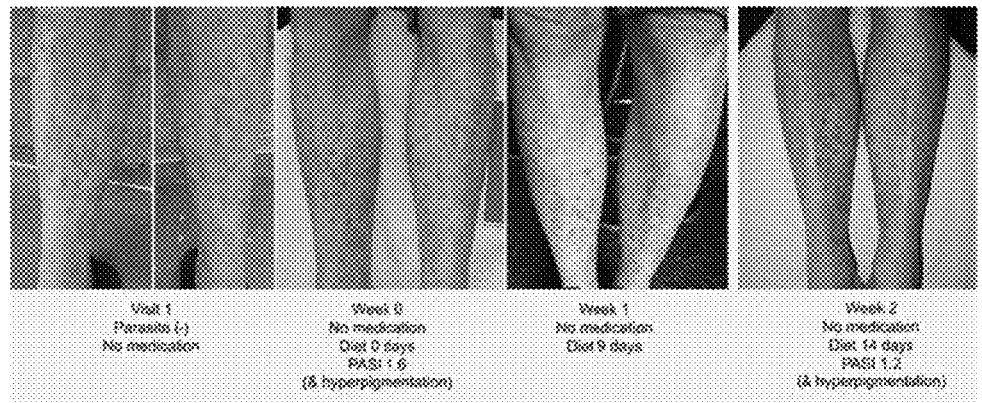
FIG. 16 shows photographs of a male subject with mild psoriasis with hyperpigmentation at visit 1 (parasite (−); no medication), week 0 (no medication; diet 0 days; PASI 1.6 (& hyperpigmentation)), week 1 (no medication; diet 9 days) and week 2 (no medication; diet 14 days; PASI 1.2 (& hyperpigmentation)). The overall PASI score for the subject decreased from 1.6 to 1.2.
Figure 17:
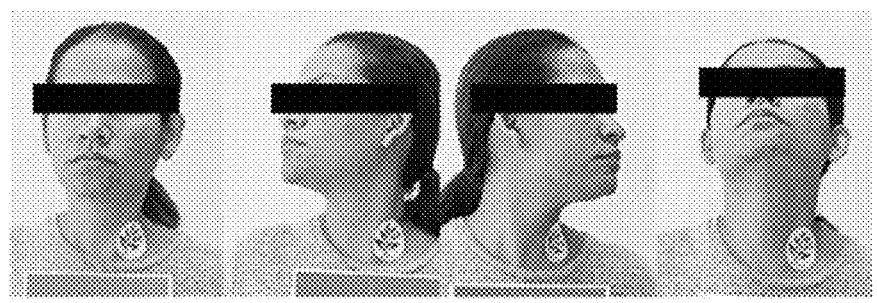
FIG. 17 shows photographs of a subject with rosacea at week 0 (no medication; diet 0 days; PASI 1.6 (& hyperpigmentation)), week 1 (no prescribed medication; diet 0 days) and week 2 (no prescribed medication; diet 14 days). The overall IGA score for the subject decreased from 3 to 2.
Figure 17:
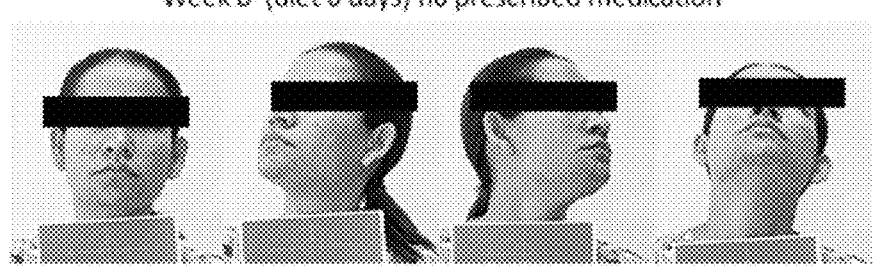
Figure 18A:
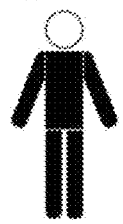
FIG. 18A shows PASI-Psoriasis Area and Severity Index (0-72) Reference: http://pasi.corti.li in the head area of a patient.
Figure 18B:
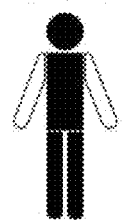
FIG. 18B shows PASI-Psoriasis Area and Severity Index (0-72) Reference: http://pasi.corti.li in the area of a patient.
Figure 18C:
FIG. 18C shows PASI-Psoriasis Area and Severity Index (0-72) Reference: http://pasi.corti.li in the trunk area of a patient.
Figure 18D:
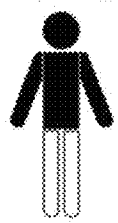
FIG. 18D shows PASI-Psoriasis Area and Severity Index (0-72) Reference: http://pasi.corti.li in the legs area of a patient.

In embodiments, the system 100 may be implemented across a communications network such as a local area network or the internet (FIG. 2). The system 100 comprises a subject location 102, a communication device 104 at the subject location 102, the communication device 104 comprising a display 106 and a user interface 108 displayable on the display 108. A server 110 is located at a server location 112 which is remote from the subject location 102. The server 110 comprises a database 114 comprising a list of food products and information relating to the content of fructose, oligosaccharides and/or polyol sugars in each of the food products and a processor 116 for calculating the total content of fructose, oligosaccharides and/or polyol sugars contained in the food product(s) on a daily diet list selected by a subject using the user interface 16 and comparing the total content of fructose, oligosaccharides and/or polyol sugars to a threshold daily value. A communications link 118 between the communication device 104 and the server 110 allows the subject to select one or more food product(s) using the user interface 108 and receive an output as to whether consumption of the food product(s) on the daily diet list are likely to prevent or control an inflammatory skin disorder in the subject.

The present invention also provides a database of information relating to the content of fructose, oligosaccharides and/or polyol sugars in a plurality of food products residing on a server computer; a user interface accessible by a subject and in communication with the database via a communication device, the user interface allowing the subject to select one or more food product(s) from the database; a processor for calculating the total content of fructose, oligosaccharides and/or polyol sugars in the selected one or more food product(s); and an output for displaying the total content of fructose, oligosaccharides and/or polyol sugars in the selected one or more food product(s) to the subject.

In embodiments, the methods include ordering at least some of the food product(s) in the customised daily diet for the subject. In embodiments, the ordering comprises communicating the food product(s) order to a merchant remote from the communication device. In embodiments, the ordering also comprises ordering the food product(s) from the food product(s) order from a production facility; producing the food product(s); and shipping the food product(s) to the subject.

EXAMPLES

Elimination Diet for the Control of Eczema (Atopic Dermatitis), Rosacea or Psoriasis (E-R-P)

The gut microbiome can elicit an inflammatory response in some individuals when an excess of specific simple sugars are consumed as part of the daily diet. This was first shown with fructose sensitivity in 1956 (Chambers et al., The Lancet 18 Aug., 1956) and in 2009 (Gibson et al., *Journal of Gastroenterology and Hepatology* 25 (2010) 252-258: doi 10.1111/j.1440-1746.2009.06149.x) research showed that simple sugar groups can contribute to Irritable Bowel Syndrome (IBS).

Building on this earlier research, a non-randomized, prospective observational dietary study was undertaken to examine if the development of common skin diseases Eczema (atopic dermatitis), Rosacea or Psoriasis (E-R-P) could be related to the mal-absorption in the small intestine of three simple sugar groups found in everyday foods (fructose, oligo-saccharides and polyols).

In the context of this study these skin diseases are viewed as a low-grade inflammatory condition; and where 'eczema' is a clinically interchangeable term with atopic dermatitis.

Informed Consent

This study was undertaken in cooperation with Lao National Dermatology Center (NDC) in Vientiane, Lao PDR. A Lao cohort is advantageous as their regular diet is already low in the sugars under review, and a higher dietary adherence and therefore validation of clinical outcomes is better assured. Subjects attended a group information session describing the procedure for the dietary intervention and signed Informed Consent.

Apart from the provision of prepared meals over a 14-day period no other intervention (pharmaceutical/OTC preparation) formed part of the study. Subjects maintained their usual skin care regimen for the study period including continued use of medications prescribed to subjects recruited via the NDC.

Recruitment

Subjects were adult volunteers recruited as out-patients from NDC, or via word of mouth. All meals, consultations, stool exams and anti-helminthic treatment were provided free of charge to participating subjects for a total of 14-days.

Subjects formally diagnosed by NDC dermatologists with any of the three diseases (E-R-P) were supplied with prepared meals together with dietary advice to ensure that the cumulative consumption per individual of the target three sugar groups was below 40 g per day throughout the 14-day period.

Out-patients from NDC were prescribed appropriate medication according to the Lao national Standard Treatment Guidelines. This may have included topical preparations containing salicylic acid, anti-histamine or cortisone creams, or similar. Subjects were asked to use medicines prescribed by NDC for a minimum of five days prior to Day 1 and continue throughout the intervention as a comparison.

Inclusion and exclusion criteria is tabled in Annex 1.

Background Clarification with Respect to FODMAP

Gibson et al published their research in 2008 related to Irritable Bowel Syndrome (IBS) where they coined and trademarked the acronym FODMAP (Fermentable Oligo, Di-, Mono-saccharides And Polyols).

The FODMAP™ grouping according to Gibson et al comprises;

short chain oligo-saccharide polymers of fructose (fructans)
galactooligosaccharides (GOS, stachyose, raffinose)
disaccharides (lactose)
monosaccharides (fructose)
sugar alcohols (polyols) such as sorbitol, mannitol, xylitol, and maltitol).

For clarification, this dietary study was not a review of IBS but was an exercise to examine dietary exclusion on dermatological diseases.

In further contrast to FODMAP™ the study did not limit lactose sugars (dairy foods) as part of the meal plan.

A maximum cumulative total of (<40 g) simple sugars (fructose, oligio-saccharides and polyols) was established per individual, per day for clinical effect.

Background Clarification with Respect to Low-Glycemic Foods

Consumption of high-glycemic foods have been associated with insulin resistance and metabolic syndrome, potentially leading to (for example) type I diabetes or hypertension/heart disease.

This dietary study did not restrict high-glycemic foods, or examine the effects of insulin resistance or metabolic syndrome. White rice (a high-glycemic food) formed part of the daily meal plan.

Methodology

Subjects were assessed for short-listing using the inclusion criteria and details were recorded via a spreadsheet. Translations of all information/materials were supplied in English and Lao language as necessary.

Adult subjects were selected to increase the likelihood of dietary adherence, with the added benefit of them having a more established and routine skin care regimen. Subjects were asked not to change their usual topical treatment regimen prior to and throughout the study period, and to continue (as necessary) using medications prescribed by NDC prior to Day 1.

Subjects confirmed free from parasites were included in the study and were examined by a dermatologist at NDC to determine the severity of eczema, psoriasis or rosacea using the EASI (Eczema Area and Severity Index (0-72); https://www.dermnetnz.org/topics/easi-score/); PASI (Psoriasis Area and Severity Index (0-72); http://pasi.corti.li); and IGA (Investigator Global Assessment (1-5); persistent erythema & papules/pustules) scales (refer Annex 2) at baseline and at Day 14. Photographs were taken of subjects on Day 1 and Day 14 by a professional photographer, and at other intervals by the study investigator.

Explanation of the study objectives and procedures was provided on Day 1 with an opportunity for questions and answers in a group setting. A picture booklet was supplied to subjects to help them identify the types of foods/beverages high (and low) in the target simple sugars that may be contributing to their skin problem. Provision of this booklet ensured all subjects received the same dietary information. No further instruction related to foods/beverages was given to subjects after Day 1 with any queries to be resolved by referencing the picture booklet.

General information was supplied as needed to all subjects via WhatsApp group chat.

Parasite Exam

Subjects supplied stool samples in the week leading up to Day 1 to be checked for intestinal parasites at NDC microbiology laboratory. Medication for those subjects (n=2) with a positive stool exam was provided at least five days prior to Day 1 and were permitted to continue in the study. Follow-up stool exams for all subjects were done on Day 7 and Day 14 repeated the above process. All subjects were clear of intestinal parasites on Day 7 and day 14.

All anti-helminthic treatment was prescribed by NDC clinicians (Albendazole 400 mg).

Two of the six subjects were diagnosed with intestinal parasites prior to the intervention and treated accordingly by NDC.

One psoriasis subject was diagnosed with *Ancylostoma duodenale*

A second psoriasis subject was diagnosed with three parasites: *Enterobius vermicularis; Ancylostoma duodenale; & Opisthorchis viverrine*. This subject chose not to take praziquantel for liver fluke (*Opisthorchis viverrini*)

Diet Diary

A diet diary was recorded by subjects for five to ten days prior to and then maintained throughout the intervention. Subjects were not informed as to the nature of the dietary exclusion before Day 1 so as not to bias their food habits prior to baseline.

At each pick-up, all subjects completed a standard questionnaire that was recorded on an Excel spreadsheet, confirming foods, beverages or medicines consumed, as well as reported bowel frequency. Their skin was examined and their diet diaries were reviewed for completeness.

Meal Plan

Prepared food was supplied from a commercial restaurant and collected every two days by subjects at the restaurant. All subjects received the same foods from a rotating meal plan comprising a total of 20 dishes. Photographs of all foods at each pick-up were recorded.

The meal plan was developed consisted of meats, poultry, fish, eggs, rice noodles, vegetables, soups, salad. Cooked plain white rice was not supplied by the restaurant but could be prepared and consumed without restriction by individual subjects as needed. Wheat products (bread, pasta, wheat noodles), fruit, onions, mushrooms and other foods high in the target simple sugars were restricted from the meal plan, and cooked foods were prepared using canola (rapeseed) oil as needed.

It was ensured that meals were high in insoluble fibre to improve digestion, this included breakfasts of fine-cut oats and UHT low-fat milk, and snacks of nuts (almonds, cashews) popcorn, and seeds (lotus seeds, sunflower kernels) supplied on rotation. Subjects were asked to only eat the foods supplied, to restrict foods/beverages from outside sources as much as possible and to use the picture book to make choices that were low in the target sugar groups. For example, as beverages were not supplied and subjects were advised to drink water or unsweetened beverages such as tea, coffee, soda water.

The meal plan was developed to accommodate personal food preferences and exceeded the average amount of foods usually consumed per day to help achieve high dietary adherence.

Subjects review of the prepared meals was overwhelmingly positive, and based on individual diaries dietary adherence was found to be very high (>90%).

Results

| Characteristics (n = 6) | |
| --- | --- |
| Sex | 4 female/2 male |
| Age range | 30-63 |
| Nationality | 5 Lao/1 non-Lao (British) |
| Daily diet diary | Maintained prior to & throughout the intervention |
| Eczema | 1 (female) |
| Psoriasis | 4 (2 male, 2 female) |
| Rosacea | 1 (female) + Acne Vulgaris co-infection |

| Sex | Age | NDC Prescription for at least five days prior to Day 1 | Parasite exam Albendazole 400 mg prescribed by NDC (as needed) at least five days prior to Day 1 | Day 1 | Day 14 | +/− |
| --- | --- | --- | --- | --- | --- | --- |
| | | PSORIASIS (PASI) | | | PASI | |
| M | 36 | betametasone dipropionate 0.064% as needed UVB therapy | NIL | 24.2 | 12.6 | −11.6 |
| F | 63 | betametasone dipropionate 0.064% as needed fexofenadine 180 mg morn & night | Ancylostoma duodenale | 14.4 | 7.2 | −7.2 |
| F | 59 | betametasone dipropionate 0.064% as needed salicylcic acid cream 3% as needed | Enterobius vermicularis Ancylostoma duodenale Opisthorchis viverrini * Subject chose not to take medication for liver fluke | 5.6 | 2.8 | −2.8 |
| M | 58 | NIL | NIL | 1.6 | 1.2 | −0.4 |
| | | ECZEMA (EASI) | | | EASI | |
| F | 56 | betametasone dipropionate 0.064% as needed fexofenadine 60 mg morn & night ketoconazole lotion as needed | NIL | 21.6 | 0 | −21.6 |
| | | ROSACEA/Acne Vulgaris (IGA) | | | IGA | |
| F | 30 | NIL | NIL | 4 | 3 | −1 |

ANNEX 1 Inclusion/Exclusion Criteria

| Inclusion criteria | Exclusion criteria |
| --- | --- |
| Adult participants (>18 years old); resident in Vientiane city for the duration of the study period; who agreed to undertake multiple parasite exams, and to accept anti-helminth treatment prescribed by NDC if found positive for intestinal parasites; agreed to present at the designated restaurant every two days for pick-up of prepared food; agreed to pre and post intervention assessment by a NDC dermatologist and be photographed; Subjects were required to have a smart phone with a WhatsApp account. A record of food/beverage consumption recorded in personal diet diaries was required for at least five days prior to inclusion (Day 1) Out-patients recruited via NDC were required to maintain any prescribed medications for at least five days prior to Day 1 and continue this regimen throughout the diet study | The use of oral antibiotics in the previous three months; pregnancy; current viral infections such as (dengue fever, chikungunya, malaria); having another diagnosed underlying medical conditions (e.g. diabetes); other physical or mental illness; or persistent diagnosed intestinal parasite infections Also excluded were subjects: practicing restrictive diets (vegetarianism, veganism etc.); subjects with food allergies; consumption of soft drinks containing fructose in excess of 600 ml per day; excess consumption of alcohol; illicit drug use; intended continued use throughout the study period of complimentary medicines; supplements; or anabolic steroids |

ANNEX 2 Severity Scales used for Eczema, Psoriasis & Rosacea

EASI-Eczema Area and Severity Index (0-72). Reference: https://www.dermnetnz.org/topics/easi-score/

| Area Score | Percentage of skin affected by eczema in each region |
|---|---|
| 0 | No active eczema in this region |
| 1 | 1-9% |
| 2 | 10-29% |
| 3 | 30-49% |
| 4 | 50-69% |
| 5 | 70-89% |
| 6 | 90-100%: the entire region is affected by eczema |

Severity Score

Severity score is recorded for each of the four regions on the body. The severity score is the sum of the intensity scores for four signs. The four signs are:
1. Redness (erythema, inflammation)
2. Thickness (induration, papulation, swelling—acute eczema)
3. Scratching (excoriation)
4. Lichenification (lined skin, furrowing, prurigo nodules—chronic eczema).

The average intensity of each sign in each body region is assessed as: none (0), mild (1), moderate (2) and severe (3).

Rosacea—IGA—Investigator Global Assessment (Rosacea Persistent erythema & Papules/pustules). Reference: 2011 DRENO et al: Development and evaluation of a Global Acne Severity Scale (GEA Scale) suitable for France and Europe, Journal of the European Academy of Dermatology and Venereology: JEADV 2011, 25, 43-48 p45

| | | |
|---|---|---|
| 0 | Clear, No lesions | Residual pigmentation and erythema may be seen |
| 1 | Almost clear, Almost no lesions | A few scattered open or closed comedones and very few papules |
| 2 | Mild | Easily recognizable: less than have of the face is involved. A few open or closed comedones and a few papules and pustules |
| 3 | Moderate | More than half of the face is involved. Many papules and pustules, many open or closed comedones. One nodule may present |
| 4 | Severe | Entire face is involved, covered with many papules and pustules, open or closed comedones and rare nodules |
| 5 | Very severe | Highly inflammatory acne covering the face with presence of nodules |

Rosacea: common scales used. Reference: 2017 TAN et al: Updating the diagnosis, classification and assessment of rosacea: recommendations from the global ROSacea COnsensus (ROSCO) panel British Journal of Dermatology (2017) 176, pp431-438 Table 1.

| Phenotype | Scale |
|---|---|
| Flushing | FAST, GFSS |
| Persistent erythema | IGA, CEA/PSA |
| Telangiectasia | None |
| Papules/pustules | Lesion counts, IGA |
| Phymatous changes | None |
| Ocular manifestations | Pending |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The reference to any prior art in this specification is not, and should not be taken as, an acknowledgement of any form of suggestion that such prior art forms part of the common general knowledge.

REFERENCES

1. Kilkenny M, Merlin K, Plunkett A, et al: The prevalence of common skin conditions in Australian school students: acne vulgaris. Br J Dermatol 139:840-845, 1998.
2. Lello J, Pearl A, Arroll B, et al: Prevalence of acne vulgaris in Auckland senior high school students. N Z Med J 108:287-289, 1995.
3. Katzman and Logan Acne vulgaris: Nutritional factors may be influencing psychological sequelae-Medical Hypotheses (2007) 69, 1080-1084
4. Hansman FS: Biochemistry in relation to the aetiology of acne vulgaris. Aust J Dermatol 1:120-124, 1951.
5. Schaefer O: When the Eskimo comes to town. Nutr Today 6:8-16, 1971.
6. Steiner PE: Necropsies on Okinawans. Anatomic and pathologic observations. Arch Pathol 42:359-380, 1946
7. Cordain L, Lindeberg S, Hurtado M, et al: Acne vulgaris: a disease of Western civilization. Arch Dermatol 138:1584-1590, 2002
8. Smith, R et al. The effect of a low glycemic load diet on acne vulgaris and the fatty acid composition of skin surface triglycerides. Journal of Dermatological Science (2008) 50, 41-52
9. Reynolds et al: Effect of Glycemic Index of Carbohydrates on Acne Vulgaris: Nutrients 2010 2, 1060-1072
10. Shepherd SJ, Gibson PR. Fructose malabsorption and symptoms of irritable bowel syndrome: guidelines for effective dietary management. J. Am. Diet. Assoc. 2006; 106:1631-9.
11. Tremellen K, Pearce K Dybiosis of Gut Mibcrobiota (DGMA)-A novel theory for the development of Polycystic Ovarian Syndrome: Medical Hypotheses 79(2012) 104-112.

What is claimed is:

1. A method for preventing or controlling rosacea, psoriasis or eczema in a subject, the method comprising administering to the subject a diet that has a cumulative daily total of 40 g or less of fructose, oligosaccharides and polyol sugars.

2. The method of claim 1 when used to control rosacea.

3. The method of claim 1 when used to control psoriasis.

4. The method of claim 1 when used to control eczema.

5. The method of claim 1, the method further comprising: obtaining dietary information from the subject wherein said dietary information includes details of the subject's diet over a period of time; assessing the dietary information to determine the total daily content of fructose, oligosaccharides and polyol sugars in the subject's diet and/or determining whether one or more foodstuffs in the subjects diet is high in fructose, oligosaccharides and polyol sugars; prescribing to the subject the diet that has a cumulative daily total of 40 g or less of fructose, oligosaccharides and polyol sugars; and administering to the subject the diet that has a cumulative daily total of 40 g or less of fructose, oligosaccharides and polyol sugars.

6. A method for treating or preventing rosacea, psoriasis or eczema in a subject, the method comprising: viewing a list of food products forming part of a diet; selecting one or more food product(s) from the list to form a daily diet list; calculating the total content of fructose, oligosaccharides and polyol sugars contained in the foodstuffs on the daily diet list; providing feedback to the subject as to whether the foodstuffs on the daily diet list contain a total amount of fructose, oligosaccharides and polyol sugars of 40 g or less per day; and, if the amount of fructose, oligosaccharides and polyol sugars in the food product(s) on the daily diet list is below 40 g or less per day, creating a customised daily diet for the subject; and administering to the subject the customised daily diet.

7. The method of claim 6, further comprising ordering at least some of the food product(s) in the customised daily diet for the subject.

8. The method of claim 6, wherein the list of food products forming part of the diet are contained on a database of information relating to the content of fructose, oligosaccharides and polyol sugars in the food products; the database residing on a server computer; a user interface accessible by a subject and in communication with the database via a communication device, the user interface allowing the subject to select one or more food product(s) from the database; a processor for calculating the total content of fructose, oligosaccharides and polyol sugars in the selected one or more food product(s); and an output for displaying the total content of fructose, oligosaccharides and polyol sugars in the selected one or more food product(s) to the subject.

* * * * *